United States Patent
Reddy et al.

(10) Patent No.: US 11,872,212 B2
(45) Date of Patent: Jan. 16, 2024

(54) SELF-HEALING ORGANIC CRYSTALS

(71) Applicant: Indian Institute of Science Education and Research (IISER) Kolkata, West Bengal (IN)

(72) Inventors: Chilla Malla Reddy, Kolkata (IN); Surojit Bhunia, Kolkata (IN); Rituparno Chowdhury, Kolkata (IN); Ishita Ghosh, Kolkata (IN)

(73) Assignee: Indian Institute of Science Education and Research (IISER) Kolkata, Mohanpur (IN)

( * ) Notice: Subject to any disclaimer, the term of this patent is extended or adjusted under 35 U.S.C. 154(b) by 0 days.

(21) Appl. No.: 17/873,246

(22) Filed: Jul. 26, 2022

(65) Prior Publication Data
US 2023/0051178 A1  Feb. 16, 2023

(51) Int. Cl.
*C07D 403/06* (2006.01)
*C07C 229/60* (2006.01)
*A61K 31/417* (2006.01)

(52) U.S. Cl.
CPC .................. *A61K 31/417* (2013.01)

(58) Field of Classification Search
CPC ........................ C07D 403/06; C07C 229/60
See application file for complete search history.

(56) References Cited

PUBLICATIONS

Peori et al., An X-Ray Crystallographic Study of the Novel Aminal bis-(p-Ethoxycarbonylphenylamino-)methane, Journal of Chemical Crystallography, vol. 39, No. 3, pp. 178-181. (Year: 2009).*
Bhunia et al., Supplementary Materials for Autonomous self-repair in piezoelectric molecular crystals, Science, vol. 373, No. 6552, pp. 321-327. (Year: 2021).*

* cited by examiner

*Primary Examiner* — Brenda L Coleman
(74) *Attorney, Agent, or Firm* — Dority & Manning, P.A.

(57) ABSTRACT

The invention provides non-centrosymmetric organic crystals which show exceptional self-healing properties. More particularly, the present invention provides non-centrosymmetric substituted imidazole and Dialkyl 4,4'-methylenebis(azanediyl)dibenzoate Crystals and a process for preparation thereof. These highly crystalline materials, when broken into pieces, can self-propel and re-join in the blink of an eye and repair themselves so precisely that they become indistinguishable from the undisturbed materials.

12 Claims, 11 Drawing Sheets

SELF-HEALING ORGANIC CRYSTALS

CROSS-REFERENCE TO RELATED APPLICATION

The present application claims filing benefit of India Patent Application Number 202131033511 filed Jul. 26, 2021, the entire contents all of which are incorporated herein by reference.

TECHNICAL FIELD

The invention relates to non-centrosymmetric organic crystals which show exceptional self-healing properties. More particularly, the present invention relates to non-centrosymmetric substituted imidazole and Dialkyl 4,4'-methylenebis(azanediyl)dibenzoate Crystals and a process for preparation thereof. These highly crystalline materials, when broken into pieces, can self-propel and re-join in the blink of an eye and repair themselves so precisely that they become indistinguishable from the undisturbed materials.

BACKGROUND AND PRIOR ART

Self-healing is the ability of a material to recover and restore its pristine properties autonomously, ideally, without the need of external intervention. This is rare in synthetic materials, and even more so in crystalline and hard materials. Such a property in functional materials is highly desirable for various high-end applications. In general, all materials degrade over a period due to harsh environmental conditions or mechanical agitation, leading to generation of micro-cracks and ultimately failure of the material. Hence, periodic human intervention is required to repair or replace the materials to maintain the performance of devices. If materials can repair the damage by themselves then the durability and the cost to profit ratio can be boosted to a great extent by cutting the maintenance cost. Keeping in mind the importance of self-healing materials, various strategies have been employed to achieve self-healing in synthetic materials like polymers, hydrogels, composites, etc. Generally, the most reported self-healing materials require some sort of stimuli such as heat, light or healing agent, etc. Moreover, mostly all self-healing materials lose their usefulness when the broken pieces fall apart from each other; these pieces are needed to be kept in contact externally to initiate the healing process.

On the other hand, poor diffusion capability in compactly packed, ordered single crystals, prevents self-healing where atomically-precise long range reordering at molecular and atomic level is extremely difficult. Despite the immense potential of highly crystalline materials in numerous applications related to optical, electrical, energy, biomedical, soft-robotics, and artificial skins, self-healing property in crystals currently remains unexplored. Coupling autonomous self-healing with crystallographic precision, will immensely boost the utility of piezoelectric, ferroelectric or second harmonic generator materials as their performance vastly depends on the preservation of their non-centrosymmetric structural order. Realization of self-healing in molecular crystals would also address their typical fragile nature, which typically limits their application in devices which are prone to mechanical impact.

The self-healing phenomenon has been widely explored in mesophasic materials and polymers but there has been limited success for organic molecular single crystalline solid systems. Organic crystals do not self-heal due to internal rigidity and the difficulty in regaining the atomic level structural order at the interface of the cracked region. Only a few examples of self-healing crystals are known that need external stimuli such as heat or solvent, but they also leave scar or sign of crack during the phenomena of self-healing mainly due to incomplete repair. The extent of self-healing in single crystal is influenced by its internal crystal packing and the external conditions under which the phenomenon takes place.

Organic crystals have seamless applications to address various real life needs therefore, there is a need for organic crystalline materials that lead to appropriate realignment, resulting into a perfect self-healing with an ability to preserve its crystalline nature, preferably, without need of any external stimuli.

Therefore, the desired coupling of self-healing with crystallinity would enable a number of long-sought technologies. For instance, many microelectronic devices that function based on precision positioning require accurately oriented, highly crystalline piezoelectrics. Piezoelectric materials must withstand prolonged mechanical loading and unloading cycles; hence fracture healing ability is critical to boost their durability (*Adv. Energy Mater.* 6, 1601016 (2016). Only a handful of reports exist on self-healing in crystalline materials with little understanding of the mechanisms (Nature. 557, 86-91 (2018) and Chem. Sci. 11, 2606-2613 (2020). Self-healing of cracks occurs in hybrid macromolecular ferritin-hydrogel crystals (Nature. 557, 86-91 (2018)), however the entire process relies on a salt gradient in solution. Self-healing is reported in single crystals of soft boronic esters (with an elastic modulus, E<2 MPa), utilizing dynamic covalent chemistry under moist conditions with prolonged contact periods of ~24 hrs, yet the macroscopic cracks remain visible demonstrating the challenge of retaining the integrity in crystals (Chem. Sci. 11, 2606-2613 (2020).

Our earlier filed Indian Patent application No. 201921024663 discloses self-healing Crystals of 3,3',5,5'-Tetramethyl-4,4'-bipyrazolyl monohydrate characterized by tetragonal crystal system having primitive space group, $P4_3$ (Space Group No: 78) with unit cell parameters a/b/c (Å): 23.0906(2), 23.0906(2), 8.62170(10) and a, (3, γ (θ°): 90, 90, 90, and a process for preparation thereof.

However, self-healing in organic materials with crystallographic precession, which is highly desirable to expand their scope for many applications, remains a great challenge.

Therefore, there remains a need in the art to provide further piezoelectric organic crystals, by overcoming many of the prior art limitations, which upon mechanical fracture, recombine without any external direction, autonomously self-heal in milliseconds with crystallographic precision.

OBJECTIVES OF THE INVENTION

It is therefore an objective of the invention to provide piezoelectric organic crystals, which upon mechanical fracture, recombine without any external direction, autonomously self-heal in milliseconds with crystallographic precision.

SUMMARY OF THE INVENTION

In line with the above objective, the invention provides non-centrosymmetric organic crystals which show exceptional self-healing properties.

In an aspect, the invention provides non-centrosymmetric organic crystals selected from substituted imidazole and Dialkyl 4,4'-methylenebis(azanediyl)dibenzoate Crystals which has self-healing properties.

In another aspect, the invention provides a process for preparation of these crystals which comprises; dissolving the substituted imidazole and Dialkyl 4,4'-methylenebis (azanediyl)dibenzoate compound in a dust free organic solvent and slowly evaporating the solvent to obtain the respective crystals.

The organic solvent may be selected from C1 to C4 alcohol or DCM.

The slow evaporation process can be aerial evaporation at ambient temperature or evaporation on warm hot plate at a temperature range of 35-40° C.

The substituted imidazole noncentrosymmetric organic crystal is 4,4''-methanediylbis-(2-ethyl-5-methyl-1H-imidazole).

Dialkyl 4,4'-methylenebis(azanediyl)dibenzoate noncentrosymmetric organic crystals are selected from Dialkyl 4,4'-methylenebis(azanediyl)dibenzoate compound and Dimethyl 4,4'-(methylenebis(azanediyl))dibenzoate.

The crystals thus obtained are subjected to crystal x-ray diffraction (SCXRD), SEM and confocal microscopy.

DETAILED DESCRIPTION OF THE INVENTION

Figure 1:
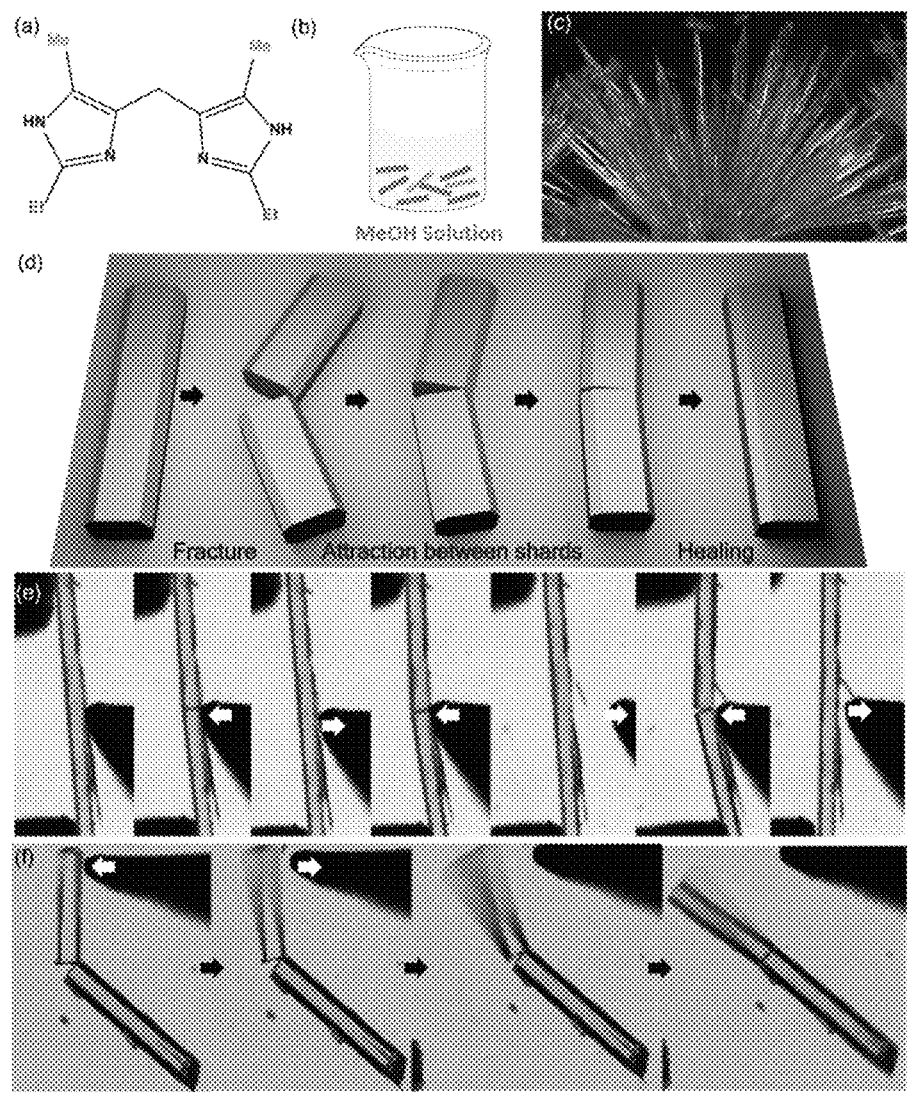
FIG. 1. Demonstration of self-healing in single crystals of system 1 (a) Molecule of 4,4'-methanediylbis-(2-ethyl-5-methyl-1H-imidazole). (b) Procedure to obtain single crystals. (c) Dark field image showing acicular single crystals under cross polarizer. (d) Schematic depiction of the application of a gentle mechanical stress resulting in fracture, followed by autonomous self-healing upon withdrawal of the force. (e) Repeat self-healing cycles in a real crystal of system 1 (f) show rapid mechanical actuation and subsequent recombination of broken shards.

The invention will now be described in detail in connection with certain preferred and optional embodiments, so that various aspects thereof may be more fully understood and appreciated.

Unless specified otherwise, all technical and scientific terms used herein have the same meaning as commonly understood by one of ordinary skill in the art, to which this invention belongs. To describe the invention, certain terms are defined herein specifically as follows.

Unless stated to the contrary, any of the words, "including", "includes", "comprising", and "comprises" mean "including without limitation" and shall not be construed to limit any general statement that it follows to the specific or similar items.

The singular forms "a," "an" and "the" include the plural, and reference to a particular numerical value includes at least that particular value unless the context clearly dictates otherwise.

As used herein, the term "or" is not meant to be exclusive and refers to at least one of the referenced components being present and includes instances in which a combination of the referenced components may be present, unless the context clearly dictates otherwise.

The terms "first," "second," and the like or any alphabetic or numeric denomination of such terms e.g. a, b, i, ii and like, herein do not denote any order, quantity, or importance, but rather are used to distinguish one element from another and intended for the purpose of orienting the reader as to specific components parts. The term "space group" is defined as symmetry group of a three-dimensional crystal pattern.

The term "non-centrosymmetric materials" as referred herein are the materials having a structure with no center of symmetry, that exhibit ferroelectricity, piezoelectricity, pyroelectricity and second-order nonlinear optical behavior.

The use of any examples or exemplary language (e.g., "such as") provided herein is intended merely to better illuminate the invention and does not pose a limitation on the scope of the invention unless otherwise claimed.

Other than in the working examples or where otherwise indicated, all numbers expressing amounts of materials, reaction conditions, time durations, quantified properties of materials, and so forth, stated in the specification and claims are to be understood as being modified in all instances by the term "about". All methods described herein may be performed in any suitable order unless otherwise indicated herein or otherwise clearly contradicted by context.

It will be understood that any numerical range recited herein includes all sub-ranges within that range and any combination of the various endpoints of such ranges or subranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

No language in the specification should be construed as indicating any non-claimed element as essential to the practice of the invention.

Accordingly, in one embodiment, the invention provides novel non-centrosymmetric organic crystals which show exceptional self-healing properties.

In an aspect, the invention provides non-centrosymmetric organic crystals which are selected from substituted imidazole and Dialkyl 4,4'-methylenebis(azanediyl)dibenzoate Crystals which has self-healing properties.

In another aspect, the invention provides a process for preparation of non-centrosymmetric organic crystals of substituted imidazole or Dialkyl 4,4'-methylenebis(azanediyl) dibenzoate compounds having exceptional self-healing properties which process comprises;

a) dissolving the substituted imidazole or Dialkyl 4,4'-methylenebis(azanediyl)dibenzoate compounds in a dust free organic solvent at a temperature of 30 to 60° C.; and b) slowly evaporating the solvent to obtain the respective crystals.

The organic solvent may be selected from C1 to C4 alcohol selected from methanol, ethanol, propanol, ter. Butanol, DCM, Chloroform, Acetonitrile or acetone. The slow evaporation process can be aerial evaporation at ambient temperature or evaporation on warm hot plate at a temperature range of 35-40° C.

The substituted imidazole non-centrosymmetric organic crystal is selected from 4,4'-methanediylbis-(2-ethyl-5-methyl-1H-imidazol e).

Dialkyl 4,4'-methylenebis(azanediyl)dibenzoate non-centrosymmetric organic crystals are selected from Diethyl 4,4'-methylenebis(azanediyl)dibenzoate compound and Dimethyl 4,4'-(methylenebis(azanediyl))dibenzoate.

The solid-state structure characterization of the said crystals is done by single crystal x-ray diffraction (SCXRD), SEM and confocal microscopy.

The crystallographic details of non-centrosymmetric organic crystals provided according to the invention are shown in below table 1.

TABLE 1

| Sample no | Compound name | Space group | Cell parameters |
|---|---|---|---|
| System 1. | 4,4'-methanediylbi s-(2-ethyl-5-methyl-1H-imidazole) Monoclinic crystal | Cc | a: 15.1991(14) b: 10.2064(11) c: 88579(9) α: 90 β: 96.8420(10) γ: 90 |
| System 2. | Diethyl4,4'-(methylenebis(azanediyl)) dibenzoate Tetragonal crystal | I4₁cd | a 20.4892(2) b: 20.4892(2) c: 8.2145(2) α: 90 β:90 γ:90 |
| System 3. | Dimethyl4,4'-(methylenebis(azanediyl)) dibenzoate Tetragonal crystal | I4₁cd | a :18 8336(4) b :18 8336(4) c :8 8097(3) α: 90 β: 90 γ: 90 |

Accordingly, the non-centrosymmetric organic crystals provided according to the invention are selected from the group consisting of a) 4,4''-methanediylbis-(2-ethyl-5-methyl-1H-imidazole) characterized by having space group, Cc with unit cell parameters a/b/c (Å):15.1991(14), 10.2064(11), 8.8579 (9) and α:90, β:96.8420(10), γ:90;

b) Diethyl 4,4'-(methylenebis(azanediyl))dibenzoate characterized by having space group, I41cd with unit cell parameters a/b/c (Å): 20.4892 (2), 20.4892 (2), 8.2145(2) and α,β, γ (θ°): 90, 90, 90; and c) Dimethyl 4,4'-(methylenebis(azanediyl))dibenzoate characterized by having space group, I41cd with unit cell parameters a/b/c (Å): 18.8336(4), 18.8336(4), 8.8097(3) and α,β, γ (θ°): 90, 90, 90.

In yet another embodiment, the non-centrosymmetric space groups, $C_c$, I4₁cd are observed in these crystals exhibit Piezoelectric characteristics.

The crystals were characterized by single crystal X-ray diffraction experiments, the self-healing properties were visualized by optical microscopy and further confirmed by SEM and confocal microscopy.

In yet another embodiment, these crystals being piezoelectric, can be used efficiently as transducer, mechanical sensors, actuators, energy harvesting devices; with the outstanding self-healing property these compounds will increase the robustness and durability many folds.

The present invention shows that these organic single crystals provide an alternative approach to self-repair, using the inherent piezoelectric effect in non-centrosymmetric structures to achieve an autonomous self-healing. These crystals have several orders of magnitude higher stiffness and hardness as compared to most other known self-healing materials (Table 1) and can autonomously recombine even when the fractured pieces are physically separated. The materials undergo self-healing within milliseconds with precise crystallographic ordering, as characterized using atomic-resolution structures obtained from single crystal X-ray diffraction and Video grabs and Confocal microscopy.

Self-Healing Phenomenon:

Self-healing behavior of the crystals of the current invention is established by breaking it into two parts with the help of a needle and tweezer, under a polarized optical microscope equipped with a high-speed camera and upon release of the stress, the two broken parts of the crystal come together instantaneously to autonomously heal by adjoining the broken pieces on the same faces on their own which leaves no visible crack when the two pieces align accurately. After the healing, the perfectly healed crystal looks alike the original one. The self-healing efficiency was verified by post-fracture SEM image of the healed crystal, which showed complete healing of mechanical deformation, as discussed herein below in the examples.

Table 2 comparison of Healing Duration of different types of self-healing materials, as shown below.

TABLE 2

| Material type | Stimuli | Healing Duration | Reference |
|---|---|---|---|
| 3,3', 5,5'-T etramethyl-4,4 -bipyrazole | Not required | milliseconds | IN201911023525 |
| Polymer | Heat | ~24 hr. | Science. 295, 1698-1702 (2002) |
| Polymer | Not required | ~40 min | Nat. Commun. 11, 1028(2020) |
| Composite | Heat | ~10 min | ACS nano, 14, 5570-5580 (2020) |

TABLE 2-continued

| Material type | Stimuli | Healing Duration | Reference |
|---|---|---|---|
| Hydrogel | — | — | Dalton Trans. 49, 5 3042-3087 (2020) |
| Single crystal | Moisture | ~24 hr. | Chern. Sci. 11, 2606-2613 (2020) |
| 4,4'-methanediylbis-(2-ethyl-5-methyl-1H-imidazole) | Not required | 1-2 milliseconds | Present work |
| Diethyl 4,4'-(methylenebis(azanediyl))dibenzoate | Not required | 1-2 milliseconds | Present work |
| Dimethyl 4,4'-(methylenebis(azanediyl))dibenzoate | Not required | 1-2 milliseconds | Present work |

Those of ordinary skilled in the art will appreciate that changes could be made to the embodiments described above without departing from the broad inventive concept thereof. It is understood, therefore, that this invention is not limited to the particular embodiments or examples disclosed herein, but is intended to cover modifications within the objectives and scope of the present invention as defined in the specification. The presented examples illustrate the invention, but they should not be considered to limit the scope of the invention in any way.

EXAMPLE(S)

Example 1/System 1

Method of preparation of Non-centrosymmetric organic crystal of Bis(2-ethyl-4-methyl-1H-imidazol-5-yl)methane:

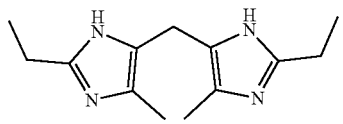 [SMILES: CCc1nc(C)c(Cc2[nH]c(CC)nc2C)[nH]1]

500 mg of Bis(2-ethyl-4-methyl-1H-imidazol-5-yl)methane was dissolved in 50 ml methanol in a clean dust free conical with warm heat on a hot plate, then kept for slow evaporation. After 4-5 days needle shape crystals obtained.

Self-Healing Property

Figure 2:
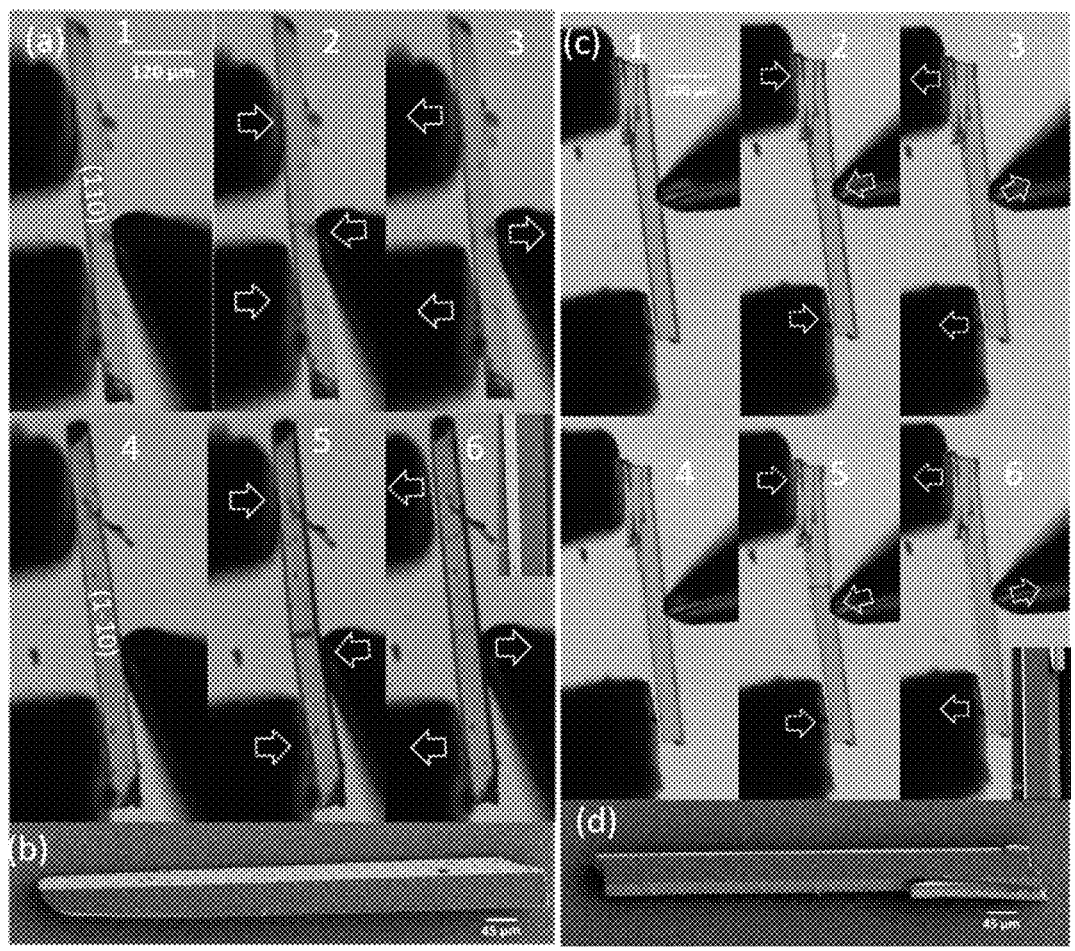
FIG. 2. (a) Face-dependent healing. Force was applied on two pairs of side faces of a same crystal in two separate experiments and corresponding SEM image (b) of healed crystal (c) repeat self-healing and corresponding SEM image (d) for crystal of system 1.

When crystal of Bis(2-ethyl-4-methyl-1H-imidazol-5-yl) methane of length 1-2 mm and width 0.1-0.25 mm was subjected to three-point bending tests by the use of a needle and a pair of forceps perpendicular to the needle direction, crystals are broken into two pieces. When force is withdrawn the broken fragments come back on their own making a high-speed motion and land on one another with great precession. The gap between the broken pieces closes instantly, and two broken crystals re-join into a single crystal which is optically indistinguishable with the pristine single crystals (FIG. 1) When a fragmented piece of the crystal is pushed closer to the broken surface of its counter piece, the fragment (generally the lighter one) jumps onto another when it approaches a critical distance. This indicates to the long range operative coulumbic attractive force at the fracture tips. Unlike other self-healing materials which completely fail when fall apart and require long mechanical compression to heal, these crystals are quite efficient in that they heal on their own without any need of compression or any kind of stimuli. The facture and healing cycles can be repeated multiple times in some cases. The monoclinic crystal system of 1 encouraged us to verify if the healing property has any face-dependent effect. We noticed the healing on both the side faces (FIG. 2). Then further we checked this healed crystal under SEM and scanned the healed sample with atomic force microscopy. We do not observe any trace of crack line in SEM, indicating perfect healing at least at topographic level (FIG. 2)

Fracture Mechanics of Bis(2-ethyl-4-methyl-1H-imidazol-5-yl)methane

Figure 3:
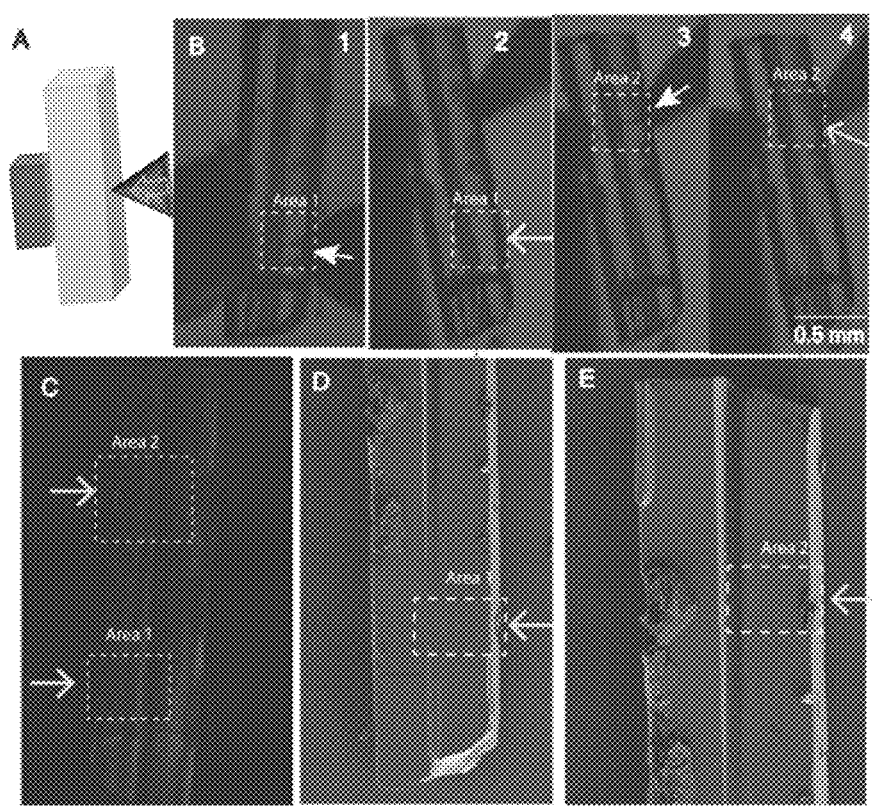
FIG. 3. Fracture in system 1 (A) Schematic of mechanical notch on the crystal (B) Self-healing of mechanical notch at different places of a crystal, confocal microscopy image (C) and SEM image (D, E) of the same crystal showing absence of any crack-line at healed area FIG. 4. Crystal Packing diagram for system 1. (a) Crystal Packing (3D H bonded network) inside the calculated BFDH morphology, where all N—H . . . N hydrogen bonded chains propagate along [101] direction. (b) Structure showing the soft zones formed by dispersive interactions/van der Waals forces among methyl and ethyl groups. (c) 1D N—H . . . N H-bonded chain FIG. 5. Simulated PXRD pattern obtained from SCRD data for system 1.

For real life applications, a material needs to undergo different levels of mechanical agitation. Here we did not limit our dimensionality of mechanical perturbation to three-point bending, we have deliberately introduced a V-shaped notch using one end of a forceps and needle head (FIG. 3). Studying the features of a crack emanating from notches under tension, tension and bending, and pure bending is very relevant to the field of fracture mechanics. It is well-known that introduction of notches results in inhomogeneous stress distribution in a material and the stress concentration factor is supposed to be maximum at the tip of the notch. The crack initiation begins from the notch introduced at the pressure point of the needle head on the single crystal. It propagates linearly through the notched crystal. The crack propagation starts from the maximum pressure point under the needle head. The video grabs show that the sharp crack passes through the width of the crystal perpendicular to the crystal needle without any deflection. Eventually upon unloading the stress, these cracks repair on their own.

Detailed video analysis in slow motion shows that when the stress is withdrawn from outside the repair process begins from the crack tip. Then gradually it occurs towards the previous needle head position. In other words, the crack closure begins from the position of the crack tip and moves inwards, repairing the crack from the tip to the loading position. It can be postulated that at the time of stress releasing the crack tip position becomes the minimum stressed point with respect to the other portion of the crack. The efficiency of the crack healing was further cross checked by SEM (FIG. 3D, E) and confocal florescence microscopy (FIG. 3C). Notably, no crack line was observed in SEM and confocal microscopic images in the cases where self-healing was near-perfect.

Crystal Structure

Figure 4:
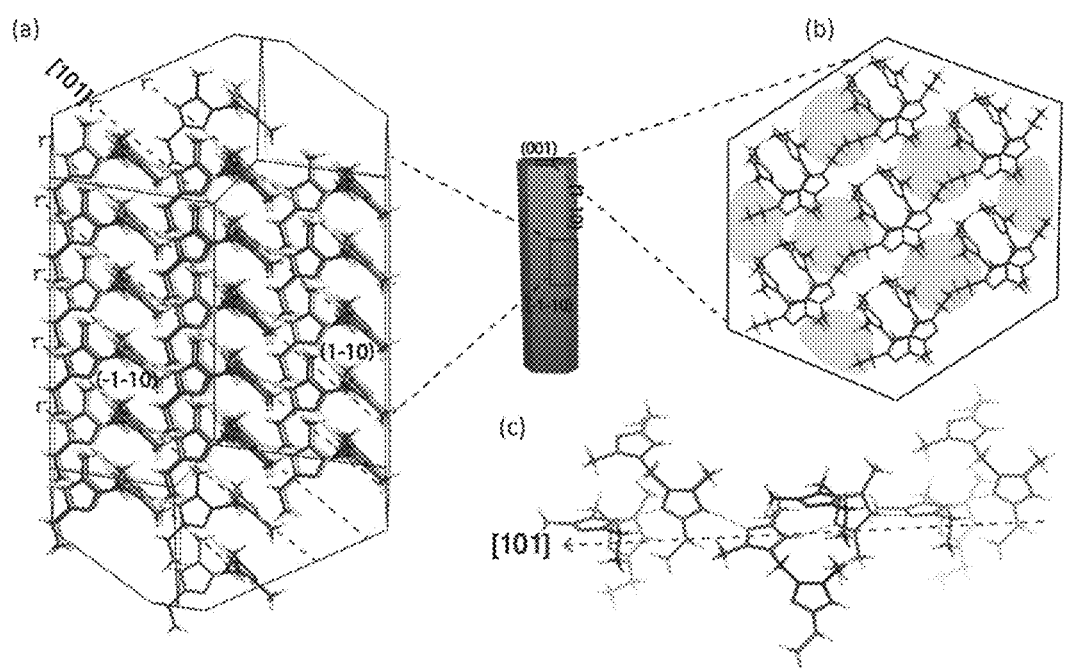

The compound 4,4"-methanediylbis-(2-ethyl-5-methyl-1H-imidazole) (system 1) crystallizes in a noncentrosymmetric polar Cc space group (monoclinic) with one molecule in the asymmetric unit. The molecule is composed of two —CH$_2$— bridged imidazole rings (FIG. 1A). In biology, imidazole heterocycle is a significant moiety which has a dipole moment of 3.61 D (along the N—H bond), can both accept and donate protons to form infinite 1D N—H N . . . H-bonded chains assembling the imidazole moieties in nearly linear fashion unless there is a steric hindrance/ hydrogen bonding from any other substituent functional groups. In this case the compound has two —$CH_2$— bridged imidazole rings (each has methyl and ethyl group as substituents) with a dihedral angle of 89.69° between them. The one part of the compound 1 engages in forming the 1D N—H N . . . H-bonded chains while the other part involves another similar parallel 1D N—H N . . . H-bonded chains. The molecules of 1 bridge several parallel 1D N—H N . . . H-bonded chains to form a 3D H bonded network (FIG. 4*a*, 4C). The parallel chains are approximately parallel to the [101] direction and form an angel of 28.42° with (001) crystallographic face (top face). In general, there is no specific polar axis for Cc crystals, and the vector of the spontaneous polarization lies on a plane perpendicular to the b-axis. Considering the dipole moment of the molecule, the spontaneous polarization of the crystal is approximately parallel to the [101] direction. The noncentrosymmetric structure definitely shows piezoelectric property, as it fulfils the space group criteria. Another important point is that, along with 3D H-bonded network, the structure has the soft zones formed by dispersive interaction/van der Waals forces among methyl and ethyl groups (FIG. 4*b*). Such softer zones are prone to local level plastic deformation. One should not confuse this local plastic deformation with plastic bending (structure generally have slip planes) or rotator plastic phases (related to molecular rotations in solid-state).

Quantitative Mechanical Property: Nanoindentation

Figure 6:
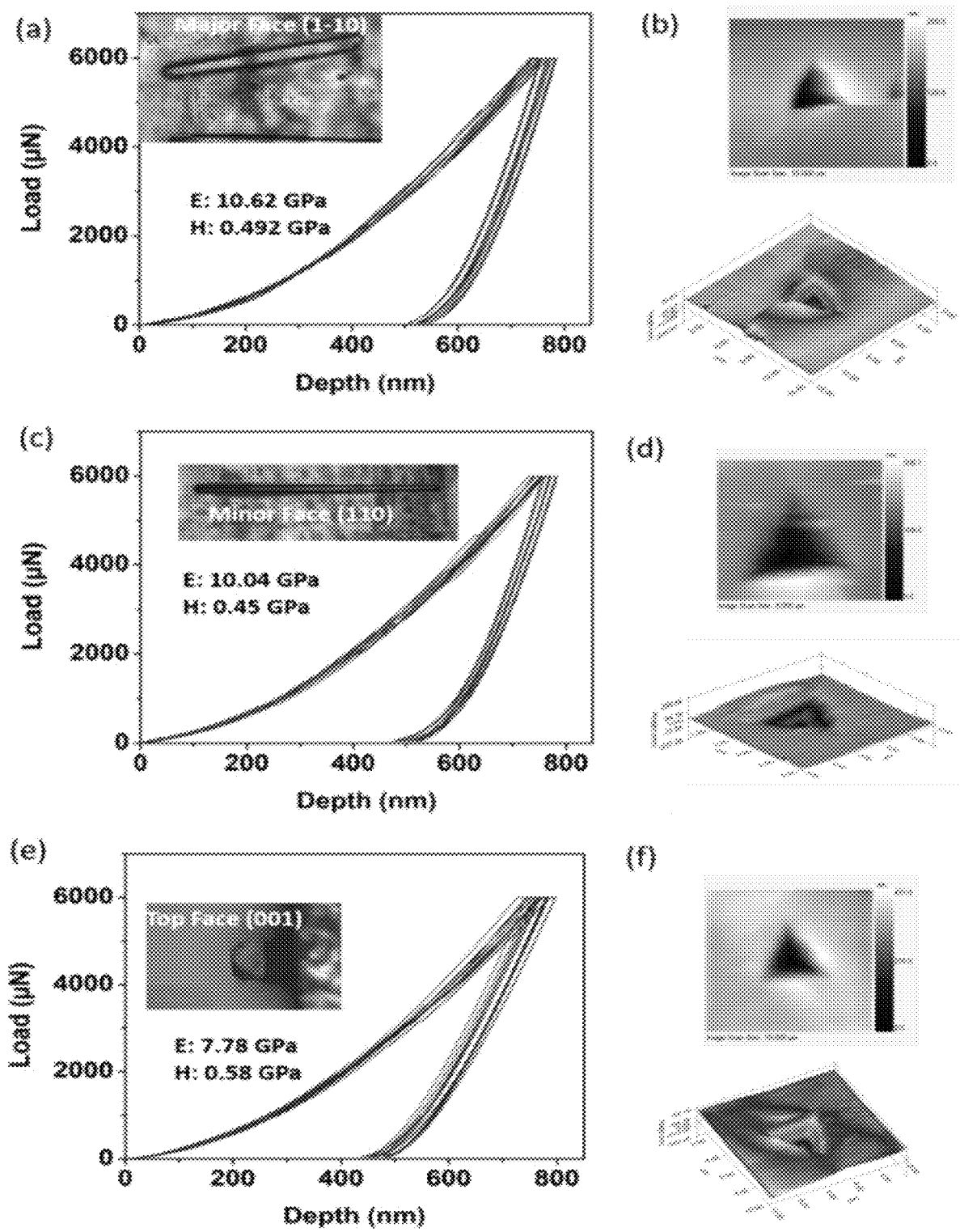
FIG. 6. Nanoindentation data on crystals of system 1. (a, c, e) Load-depth (P-h) curves from pristine crystals of 2. Crystal faces are marked in insets, (b, d, f) and the corresponding SPM images showing indent impressions FIG. 7. 2D projection of reconstructed reciprocal image between pristine (a) and completely-healed crystals (b) for crystal of system 1

In general, high mechanical strength and healing efficiencies have a tendency to be mutually exclusive. Because of the entanglement of longer polymer chains, amorphous high-molecular-weight polymers often form mechanically robust structures hence do not possess self-repairing ability except when they are melted owing to the too sluggish diffusion of entangled polymer chains. It is challenging to achieve self-healing in stiff materials. Though there is a direct correlation between healing efficiency and mechanical robustness, in crystalline materials systematic investigation is required to understand it further. We have employed nanoindentation technique which can help in quantifying the mechanical properties and extract the anisotropic mechanical behaviour information from single crystals. This crystal has multiple identified crystallographic faces, namely (1-1 0): major side face, two minor side face namely (1 1 0), (1 0 0) and top face (0 0 1) which is perpendicular to the growth axis. We have done face indexing on a reasonably good number of samples (~7 different crystals). In most cases, minor side face (001) does not appear. However, all appeared faces match with the calculated BFDH morphology obtained from experimental CIF file. We have indented on major side face (1-10), one of the minor side faces [most likely (110)] and top face (001). We have employed a maximum load of 6 mN using a Berkovich tip (radius~150 nm) on different locations on a particular type of sample (on a defined face of the single crystal) to obtain multiple load-depth (P-h) curves. Thereafter Elastic modulus (E) and Hardness (H) were extracted from the indents following standard models. Results are tabulated in the Table 2. The data suggests that the side faces are harder and stiffer than the top face (FIG. 6). It is noteworthy that the side faces are naturally grown while top face is created by freshly cleaving the crystal before the experiments to obtain a flat surface. In general, the top faces are sharp and pointed in nature, hence not suitable for direct indentation due to severely tilted faces. The anisotropy in the mechanical response from system 1 can be understood by analysing the crystal packing and energy frameworks. Along the crystal needle direction, molecules are packed by predominantly dispersion (soft) type of interactions while along the orthogonal directions the major interactions are columbic type (strong, electrostatic interactions).

TABLE 3

Experimental E and H for different faces of crystal of system 1.

| Faces | Mean Elastic Modulus(GPa) | Std. Dev. of Elastic modulus(GPa) | Mean Hardness(GPa) | Std. Dev. Of Hardness(GPa) |
|---|---|---|---|---|
| (1-10) | 9.55 | 0.24 | 0.492 | 0.021 |
| (110) | 9.03 | 0.41 | 0.453 | 0.043 |
| (001) | 6.98 | 0.33 | 0.576 | 0.029 |

Figure 7:
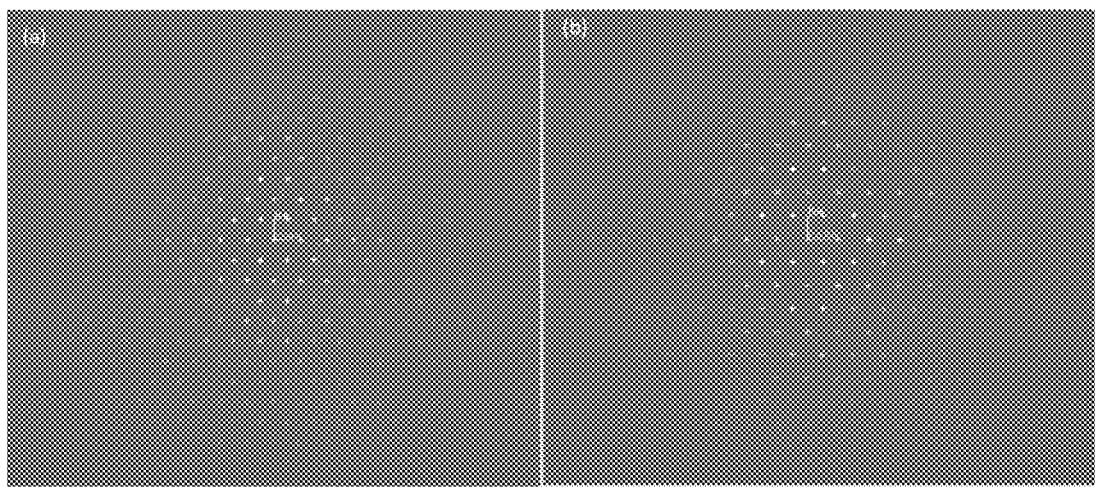

Crystallographic Precession Self-healing: The absence of the defects associated with grain boundaries in single crystals provide unique advantages, particularly mechanical, optical and electrical to use industrially in technological applications, especially in optics and electronics. And crystallinity determines all the physical properties of the crystals, therefore, it is vital to assess the crystalline order before and after healing of the crystals. We have utilized in-house diffractometer with beam size of 300 µM to compare the structural integrity of crystals, pre- and post-healing. Comparison of the diffraction profiles of the pristine crystals with the completely-healed (with no visible crack-line after healing) single crystals reveals the retention of the bulk crystallinity in the latter. Further, the indistinguishable 2D projection of reconstructed reciprocal image between pristine and completely-healed crystals indicate an efficient macroscopic domain-alignment and neat-healing at the level of crystallographic detection limit. Hence, for practical purposes, the neatly self-healed crystals can be considered as "single crystalline" (FIG. 7). Further, from a complete diffraction data from neatly-healed crystals, we obtained the structural model with excellent fit, self-healing at crystallographic level (Table. 4, 5).

Figure 5:
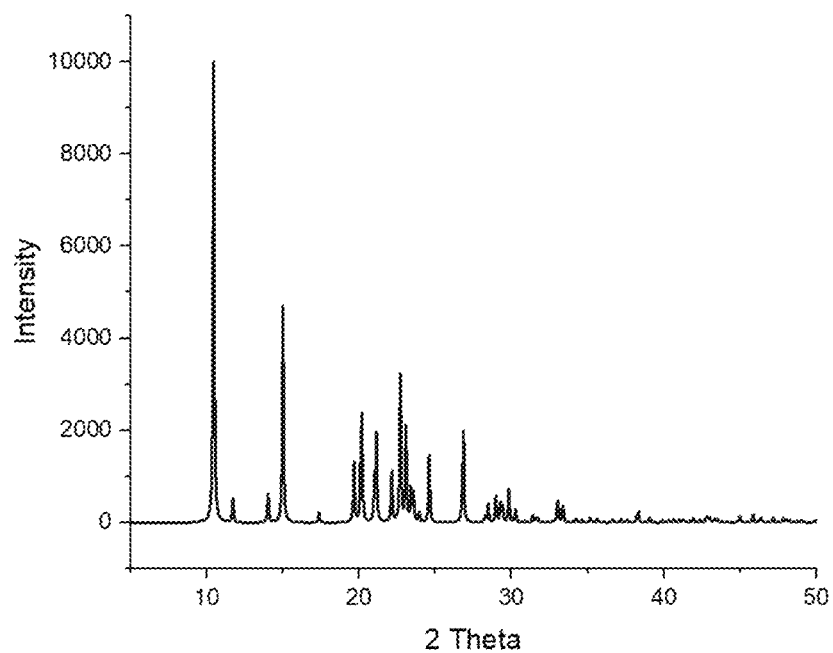

SCXRD: Cc (piezoelectric space group). Crystal structure has N—H . . . N hydrogen bonded 3D network with soft dispersive interaction zones formed by ethyl and methyl groups. The simulated PXRD pattern obtained SCRD data, is shown in FIG. 5.

TABLE 4

Comparison of crystallographic data for pristine and healed crystals for system 1.

| Sample state | Pristine | Neatly-heated |
|---|---|---|
| Formula | $C_{13}H_{20}N_4$ | $C_{13}H_{20}N_4$ |
| Crystal system | monoclinic | monoclinic |
| Space group | Cc | Cc |
| a/Å | 15.1382(2) | 15.13959(10) |
| b/Å | 9.97169(10) | 9.97289(10) |
| c/Å | 8.83449(10) | 8.83589(10) |
| α/° | 90 | 90 |
| β/° | 98.3849(10) | 98.3899(10) |
| γ/° | 90 | 90 |
| Volume/Å$^3$ | 1319.32(3) | 1319.81(2) |
| Z | 4 | 4 |
| Radiation | Cu Kα (λ = 1.54184) | Cu Kα (λ = 1.54184) |
| $\rho_{calc}$g/cm$^3$ | 1.170 | 1.169 |
| µ/mm$^{-1}$ | 0.568 | 0.568 |
| F(000) | 594.0 | 594.0 |
| 2θ range for data collection/° | 10.658 to 133.152 | 10.658 to 136.286 |
| Index ranges | −18 ≤ h ≤ 17, −11 ≤ k ≤ 11, −10 ≤ l ≤ 9 | −18 ≤ h ≤ 18, −12 ≤ k ≤ 12, −10 ≤ l ≤ 9 |
| Reflections collected | 10252 | 15794 |
| Goodness-of-fit on F$^2$ | 1.063 | 1.077 |
| Final R indexes | $R_1$ = 0.0326, w$R_2$ = | $R_1$ = 0.0306, w$R_2$ = |

TABLE 4-continued

Comparison of crystallographic data for pristine and healed crystals for system 1.

| Sample state | Pristine | Neatly-heated |
|---|---|---|
| [all data] | 0.0813 | 0.0829 |
| Temperature | 100K | 100K |

TABLE 5

Comparison of H-bonding parameters for pristine and healed crystals for system 1.

| D-H...A | d((D-H)/Å) | | d((H-A)/Å) | | d(D-A)/Å | | D-H-A/° | |
|---|---|---|---|---|---|---|---|---|
| | Pristine | Neatly healed | Pristine | Neatly healed | Pristine | Neatly healed | Pristine | Neatly healed |
| N3-H3...N2[1] | 0.90 (3) | 0.91 (3) | 2.01 (3) | 1.99 (3) | 2.888 (2) | 2.892 (2) | 167 (3) | 168 (3) |
| N1-H1-N4[2] | 0.92 (4) | 0.92 (4) | 1.89 (3) | 1.90 (4) | 2.806 (2) | 2.810 (2) | 169 (3) | 171 (3) |

1 + X, 1 − Y, 1/2 + Z; 2 − 1/2 + X, −1/2 + Y, + Z

Example 2/System 2

Method of preparation of Non-centrosymmetric organic crystal of Diethyl 4,4'-(methylenebis(azanediyl))dibenzoate:

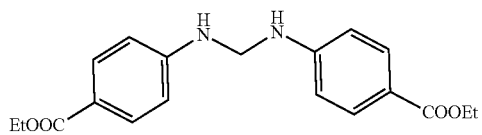 [SMILES: CCOC(=O)c1ccc(NCNc2ccc(C(=O)OCC)cc2)cc1]

400 mg of Diethyl 4,4'-(methylenebis(azanediyl))dibenzoate was dissolved in 50 ml methanol or ethanol or DCM or Chloroform or Acetonitrile or acetone in a clean dust free conical with warm heat on a hot plate, then kept for slow evaporation. After 4-7 days needle shape crystals obtained.

Figure 11:
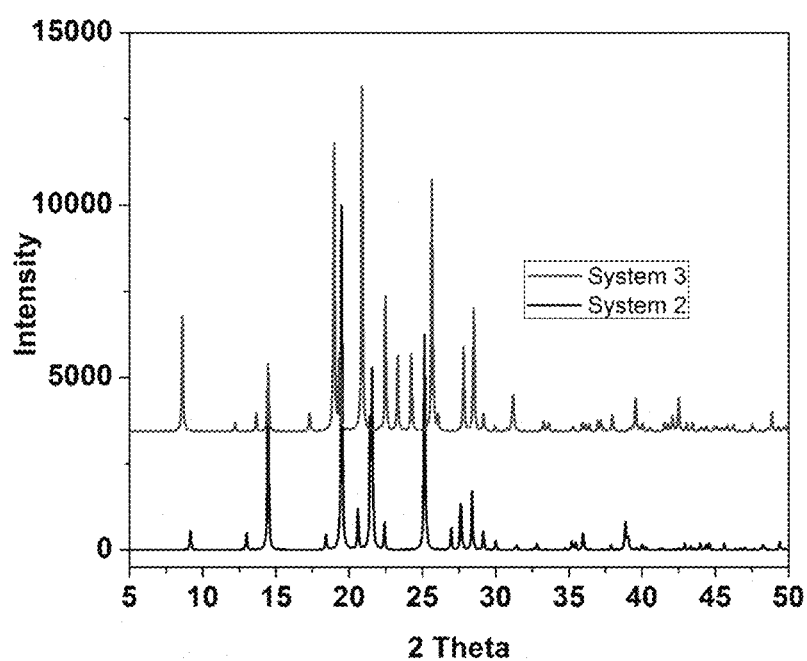
FIG. 11. Comparison of simulated PXRD patterns for system 2 and 3.

SCXRD: I41cd (piezoelectric space group). Crystal structure with C—H . . . O helical hydrogen bonded 3D network with soft dispersive interaction zone formed by ethyl groups. The simulated PXRD pattern obtained SCRD data, is shown in FIG. 11.

Example 3/System 3

Method of preparation of Non-centrosymmetric organic crystal of Dimethyl 4,4'-(methylenebis(azanediyl))dibenzoate:

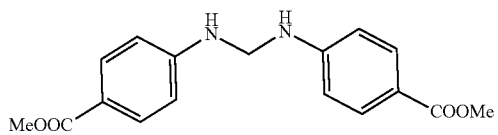 [SMILES: COC(=O)c1ccc(NCNc2ccc(C(=O)OC)cc2)cc1]

400 mg of Dimethyl 4,4'-(methylenebis(azanediyl))dibenzoate was dissolved in 50 ml methanol or ethanol or DCM or Chloroform or Acetonitrile or acetone in a clean dust free conical with warm heat on a hot plate, then kept for slow evaporation. After 4-7 days needle shape crystals obtained.

SCXRD: I4₁cd (piezoelectric space group). Crystal structure with C—H . . . O helical hydrogen bonded 3D network with soft dispersive interaction zone formed by ethyl groups.

The simulated PXRD pattern obtained SCRD data, is shown in FIG. 11.

Figure 8:
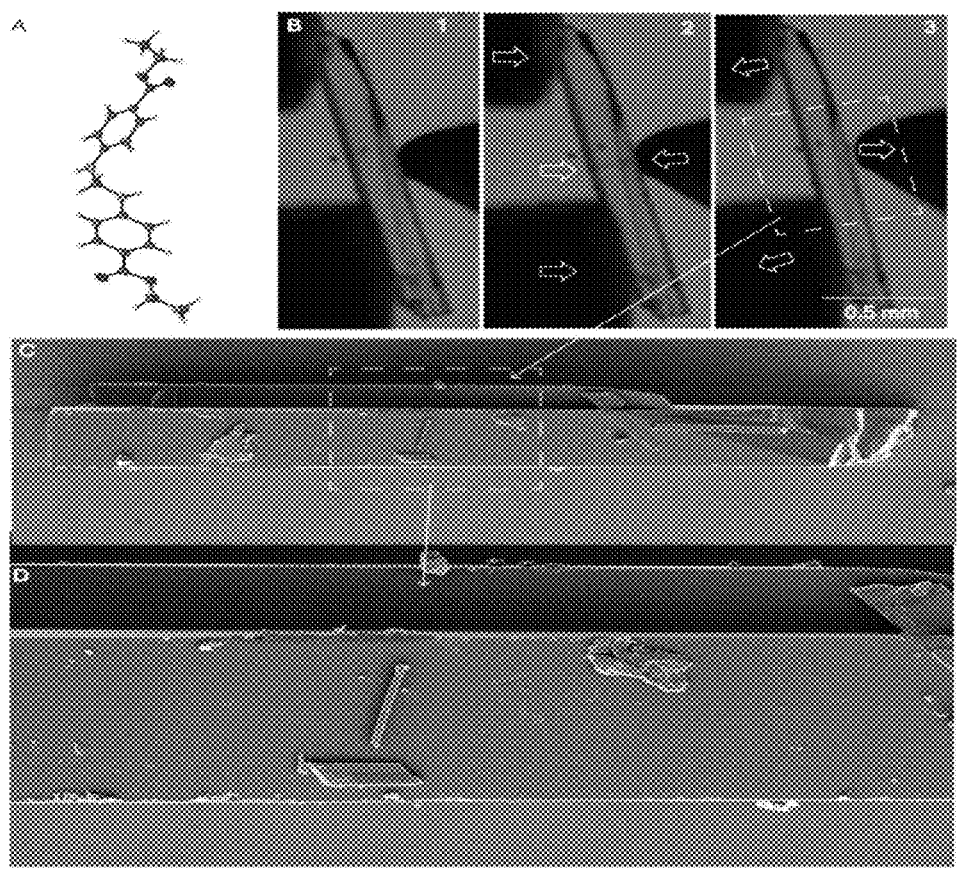
FIG. 8. A) ORTEP diagram of system 2. B) Video grab showing the self-healing phenomenon with healing time 1-2 ms. (D-E) SEM image of the healed crystal showing perfect healing.
Figure 9:
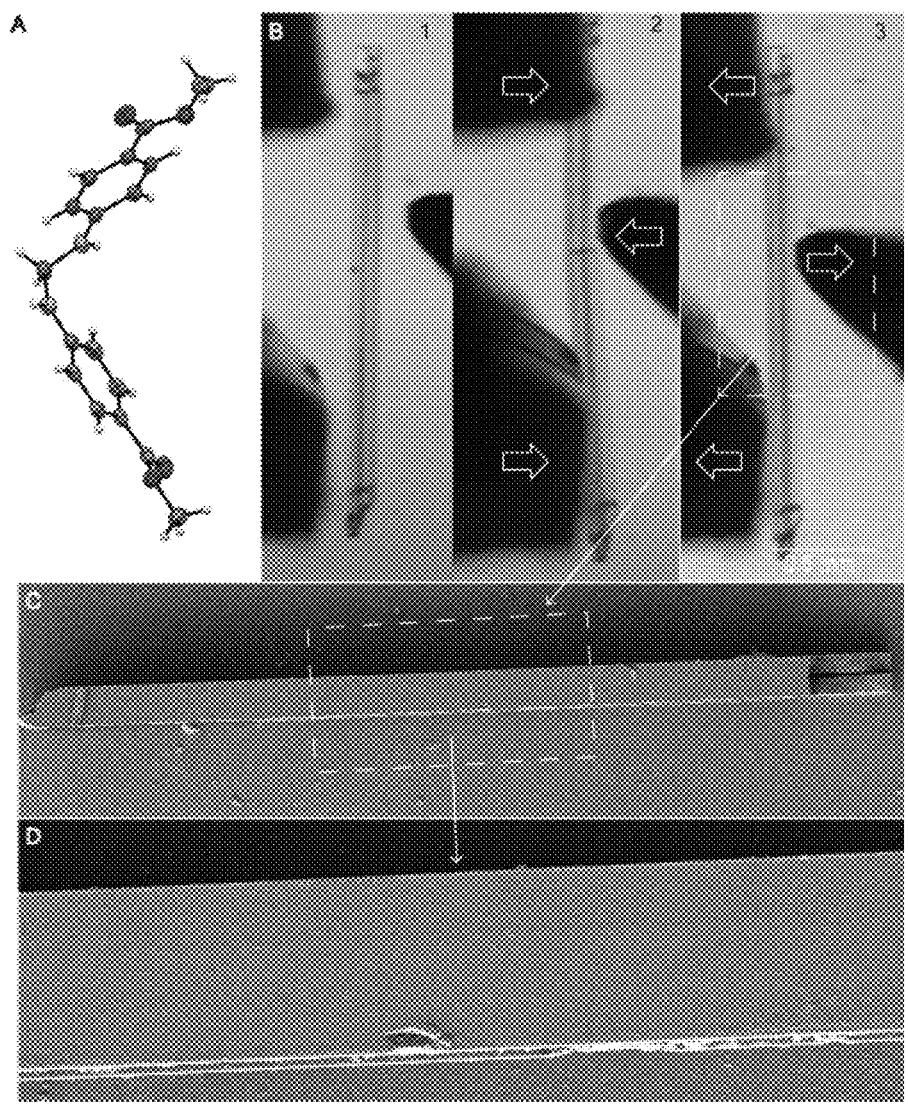
FIG. 9. A) ORTEP diagram of system 3. B) Video grabs showing the self-healing phenomenon with healing time 1-2 ms. (D-E) SEM image of the healed crystal showing perfect healing.

Demonstration of Self-healing: Clean, defect-free single crystals of systems 2 and 3 with average dimensions of (1 mm×0.07 mm×0.05 mm) were picked and subjected to three-point bending tests on a glass slide support under a stereo-microscope equipped with a high-speed camera. Crystals under excessive mechanical stress fracture in brittle manner without any sign of noticeable plastic deformation at macroscopic scale. On application of a gentle force, the crystals generally broke with linear cracks; upon withdrawal of the force the broken fragments attracted each other due to a strong force which helps in the rejoining process. It has been observed a perfect healing with no sign of cracks in some cases when the two broken ends self-align and close the gap with precision. Such perfectly-healed crystals looked similar to the pristine ones under the microscope. However, in most cases the landing of pieces was not perfect due to fast attractive motion of the broken pieces or uneven fracture surfaces, leading to misalignment. In such cases, a visible crack-line remained at the joint. The crystals with visible crack line were still capable of holding together and behaved like a monolithic sample when moved on a glass slide using tweezers. The healed sample when observed under SEM, there was no presence of crack-line, confirming the efficient healing (FIG. 8, 9)

Figure 10:
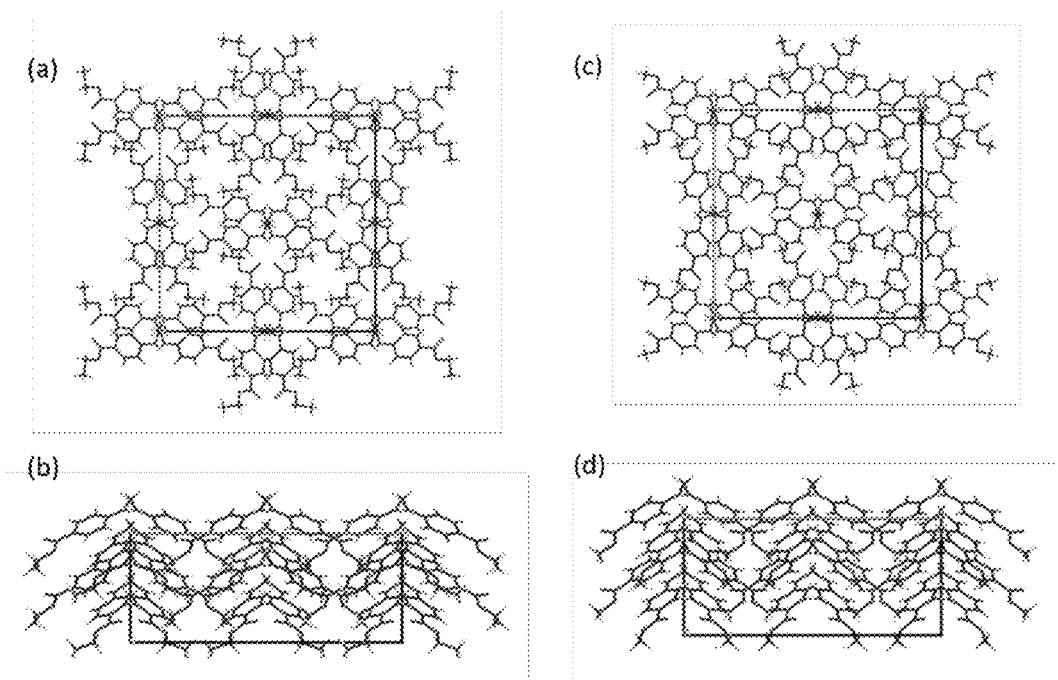
FIG. 10. Comparison of crystal packing in along different directions for system 2(a. b) and 3 (c, d).

Crystal Structure: To establish structural basis for the self-healing and mechanical actuation response of examples 2 and 3, the crystal structure was determined and analysed the packing (FIG. 10). They both crystallizes in the tetragonal non-centrosymmetric polar space group I4₁cd with half molecule in the asymmetric unit. The crystals of examples 2 and 3 have very similar structure and exhibit similar self-healing property (table 6). Although the two structures appear very similar, the simulated PXRD patterns do not match exactly (FIG. 11). Due to the presence of a sp³-hybridized, tetrahedral methylene connector (—CH₂—), the molecule adopts a 'V-shaped' geometry, with an angle between the two arms for the crystal of example 2: 110.5° and for the crystal of example 3: 105.48°. These 'V-shaped' molecules, which sit on a two-fold axis, close pack along c-axis with a criss-cross arrangement and form columns. Notably, the molecules do not involve in π-stacking interactions, instead interact via weak C—H . . . π(for system 2: d [Å], θ [°]: 2.61 Å, 153.6°/for system 3: d [Å], θ [°]: 2.92 Å, 166.20°). With the —CH₂— groups of all the V-shaped molecules in columns pointed to the same side, the net dipole moment is expected to orient along the crystal needle axis, i.e. c-axis here. Each molecule contains two potential hydrogen bond donors, namely N—H groups at the mid-region and two hydrogen bond acceptors, namely —C=O groups of —COOMe/—COOEt functionalities, at either ends of the molecule. The molecules from parallel columns are connected by strong N—H . . . O (for system 2: d [Å], θ [°]: 2.12 Å; 155.73° for system 3: d [Å], θ [°]: 2.03 Å,163.82° (amine-to-ester) and supportive C—H . . . O (for system 2: d [Å], θ [°]: 2.57 Å, 135.37°/for system 3: d [Å], θ[°]: 2.49 Å, 140.15°) interactions, and form a three-dimensional (3D) hydrogen bonded network. Besides, the structure does not have any flat slip planes but has dispersive interaction zones in the crystal-packing. Hence the overall density of hydrogen bonds in the structure is moderate with interaction strength comparable in three dimensions.

TABLE 6

Crystalligraphic details for sysytem 2 and 3.

| Sample no | Compound name | Space group | Cell parameters | Isostructurality index |
|---|---|---|---|---|
| System 2 | Diethyl 4,4'-(methylenebis(azanediyl)) dibenzoate | I4$_1$cd | a: 20.4892(2)<br>b: 20.4892(2)<br>c: 8.2145(2)<br>α: 90 β: 90 γ: 90 | $\prod = \left\| \frac{a+b+c}{a'+b'+c'} \right\| - 1$<br>$= 0.04$ |
| System 3 | Dimethyl 4,4'-(methylenebis(azanediyl) dibenzoate | I4$_1$cd | a: 19.25900(10)<br>b: 19.25900(10)<br>c: 8.69590(10)<br>α: 90 β: 90 γ: 90 | |

We claim:

1. A process for the preparation of non-centrosymmetric organic crystals of substituted imidazole or dialkyl 4,4'-methylenebis (azanediyl)dibenzoate compounds, which process comprises;
    a) dissolving the substituted imidazole or dialkyl 4,4'-methylenebis (azanediyl)dibenzoate compounds in a dust free organic solvent at a temperature of 30 to 60° C.;
    b) slowly evaporating the solvent to obtain the respective crystals; and
    c) fracturing the crystals by a three-point bending test into pieces wherein the pieces self-propel without external direction and recombine;
    wherein the non-centrosymmetric organic crystals are selected from the group consisting of
        a) 4,4'-methanediylbis-(2-ethyl-5-methyl-1H-imidazole);
        b) diethyl 4,4'-(methylenebis(azanediyl))dibenzoate; and
        c) dimethyl 4,4'-(methylenebis(azanediyl))dibenzoate.

2. The process as claimed in claim 1, wherein, the substituted imidazole non-centrosymmetric organic crystal is 4,4"-methanediylbis-(2-ethyl-5-methyl-1H-imidazole).

3. The process as claimed in claim 1, wherein, the dialkyl 4,4'-methylenebis(azanediyl)dibenzoate non-centrosymmetric organic crystals are selected from diethyl 4,4'-methylenebis(azanediyl)dibenzoate compound and dimethyl 4,4'-methylenebis(azanediyl))dibenzoate.

4. The process as claimed in claim 1, wherein, the non-centrosymmetric organic crystals are selected from the group consisting of—
    a) 4,4'-methanediylbis-(2-ethyl-5-methyl-1H-imidazole) characterized by having space group, Cc with unit cell parameters a/b/c (Å):15.1991(14), 10.2064(11), 8.8579 (9) and α:90, β:96.8420(10), γ:90;
    b) diethyl 4,4'-(methylenebis(azanediyl))dibenzoate characterized by having space group, I41cd with unit cell parameters a/b/c (Å): 20.4892(2), 20.4892(2), 8.2145 (2) and α, β, γ(θ°): 90, 90, 90;
    c) dimethyl 4,4'-(methylenebis(azanediyl))dibenzoate characterized by having space group, I41cd with unit cell parameters a/b/c (Å): 18. 8336(4), 18.8336(4), 8.8097(3) and α, β, γ(θ°): 90, 90, 90.

5. The process as claimed in claim 1, wherein, the organic solvent is selected from a C1 to C4 alcohol selected from methanol, ethanol, propanol, ter. Butanol, DCM, Chloroform, Acetonitrile or acetone.

6. The process as claimed in claim 1, wherein, the slow evaporation process can be aerial evaporation at ambient temperature.

7. The process as claimed in claim 1, wherein, the crystals being piezoelectric can be used as transducer, mechanical sensors, actuators, or energy harvesting devices.

8. The process as claimed in claim 1, wherein, the solid-state structure characterization of the said crystals is done by single crystal X-ray diffraction (SCXRD), the self-healing properties were visualized by optical microscopy and further confirmed by SEM and confocal microscopy.

9. The process as claimed in claim 1, wherein the non-centrosymmetric organic crystal is 4,4'-methanediylbis-(2-ethyl-5-methyl-1H-imidazole).

10. The process as claimed in claim 1, wherein the non-centrosymmetric organic crystal is diethyl 4,4'-(methylenebis(azanediyl))dibenzoate.

11. The process as claimed in claim 1, wherein the non-centrosymmetric organic crystal is dimethyl 4,4'-(methylenebis(azanediyl))dibenzoate.

12. The process as claimed in claim 1, wherein, the slow evaporation process can be evaporation on warm hot plate at a temperature range of 35-40° C.

* * * * *